United States Patent
Sudharsan

(10) Patent No.: US 11,538,582 B2
(45) Date of Patent: *Dec. 27, 2022

(54) SYSTEMS AND METHODS FOR CREATING AND SELECTING MODELS FOR PREDICTING MEDICAL CONDITIONS

(71) Applicant: WellDoc, Inc., Columbia, MD (US)

(72) Inventor: Bharath Sudharsan, Baltimore, MD (US)

(73) Assignee: Welldoc, Inc., Columbia, MD (US)

( * ) Notice: Subject to any disclaimer, the term of this patent is extended or adjusted under 35 U.S.C. 154(b) by 414 days.

This patent is subject to a terminal disclaimer.

(21) Appl. No.: 16/857,880

(22) Filed: Apr. 24, 2020

(65) Prior Publication Data

US 2020/0251200 A1    Aug. 6, 2020

Related U.S. Application Data

(63) Continuation of application No. 15/783,674, filed on Oct. 13, 2017, now Pat. No. 10,672,509, which is a (Continued)

(51) Int. Cl.
*G16H 40/67* (2018.01)
*G16H 50/50* (2018.01)
(Continued)

(52) U.S. Cl.
CPC .............. *G16H 40/67* (2018.01); *G06N 5/04* (2013.01); *G06N 5/048* (2013.01); *G16H 20/10* (2018.01);
(Continued)

(58) Field of Classification Search
None
See application file for complete search history.

(56) References Cited

U.S. PATENT DOCUMENTS 5,769,074 A    6/1998    Barnhill et al.
7,447,643 B1   11/2008   Olson et al.
(Continued)

FOREIGN PATENT DOCUMENTS

EP    1309271 A1    5/2003
WO    2002015777 A1    2/2002
(Continued)

OTHER PUBLICATIONS

Healthways—The Solution for Well-Being Improvement, www.Healthways.com/PositiveChange (6 pgs.).
(Continued)

*Primary Examiner* — Alan Chen
(74) *Attorney, Agent, or Firm* — Bookoff McAndrews, PLLC

(57) ABSTRACT

Systems and methods are provided for selecting one or more models for predicting medical conditions. An exemplary method may include receiving data related to a patient and extracting metadata from the received data. The method may further include selecting the one or more models from a library of models based on the extracted metadata and applying the selected one or more models. The method also may include generating a notification when the application of the selected one or more model indicates an intervention is necessary.

20 Claims, 5 Drawing Sheets

Related U.S. Application Data continuation of application No. 14/315,053, filed on Jun. 25, 2014, now Pat. No. 9,824,190.

(60) Provisional application No. 61/839,528, filed on Jun. 26, 2013.

(51) Int. Cl.
    *G16H 50/70* (2018.01)
    *G16H 50/20* (2018.01)
    *G16H 40/20* (2018.01)
    *G16H 40/63* (2018.01)
    *G06N 5/04* (2006.01)
    *G16H 20/10* (2018.01)

(52) U.S. Cl.
    CPC .............. *G16H 40/20* (2018.01); *G16H 40/63* (2018.01); *G16H 50/20* (2018.01); *G16H 50/50* (2018.01); *G16H 50/70* (2018.01)

(56) References Cited

U.S. PATENT DOCUMENTS

| | | | |
|---|---|---|---|
| 7,769,600 B2 | 8/2010 | Iliff | |
| 7,801,836 B2 | 9/2010 | Sureka | |
| 8,034,558 B2 | 10/2011 | Smith et al. | |
| 8,036,915 B2 | 10/2011 | Kremer et al. | |
| 8,140,270 B2 | 3/2012 | Kingsmore et al. | |
| 8,838,513 B2 | 9/2014 | Sudharsan | |
| 10,672,509 B2 * | 6/2020 | Sudharsan | G06N 5/04 |
| 2002/0026103 A1 | 2/2002 | Norris et al. | |
| 2003/0208113 A1 | 11/2003 | Mault et al. | |
| 2004/0199482 A1 | 10/2004 | Wilson | |
| 2005/0086082 A1 | 4/2005 | Braunstein et al. | |
| 2008/0228043 A1 | 9/2008 | Kenedy et al. | |
| 2009/0030290 A1 | 1/2009 | Kozuch et al. | |
| 2010/0324936 A1 | 12/2010 | Vishnubhatla et al. | |
| 2011/0225112 A1 | 9/2011 | Cameron et al. | |
| 2014/0118138 A1 | 5/2014 | Cobelli et al. | |
| 2015/0018633 A1 | 1/2015 | Kovachev et al. | |

FOREIGN PATENT DOCUMENTS

| | | |
|---|---|---|
| WO | 2006072011 A2 | 7/2006 |
| WO | 2007143083 A2 | 12/2007 |
| WO | 2008103827 A1 | 8/2008 |
| WO | 2011112974 A1 | 9/2011 |

OTHER PUBLICATIONS

Hilario, M. et al., "A Data Mining Ontology for Algorithm Selection and Meta-Mining," Proc. of the ECML/PKDD 2009 Workshop on Third Generation Data Mining: Towards Service-Oriented Knowledge Discovery (SoKD-09), pp. 76-87, 2009.

Lustria, M. L.. et al., "Computer-tailored health Interventions delivered over the web: Review and analysis of key components," Elsevier-Patient Education and Counseling, 74, pp. 156-173 (2009).

Pfahringer, B. et al., "Meta-Learning by Landmarking Various Learning Algorithms," Proc. 17th International Conference on Machine Learning, pp. 743-750, 2000.

Riley, W. T. et al., "Health behavior models in the age of mobile interventions: are our theories up to the task?" TBM, pp. 53-71.

Serban, F. et al., "A Survey of Intelligent Assistants for Data Analysis," ACM Computing Surveys, pp. 1-36, 2012.

Visweswaran, S., "Learning Patient-Specific Models from Clinical Data," ISBN: 0549455388, University of Pittsburgh, 2012.

Wagner et al., Continuous Glucose Monitoring: A review for behavioral researchers, May 2012, Psychosom Med., 74 (4), pp. 1-18 (2012).

* cited by examiner

SYSTEMS AND METHODS FOR CREATING AND SELECTING MODELS FOR PREDICTING MEDICAL CONDITIONS

CROSS-REFERENCE TO RELATED APPLICATIONS

This Application is a continuation of U.S. application Ser. No. 15/783,674, filed Oct. 13, 2017, which is a continuation of U.S. patent application Ser. No. 14/315,053, filed on Jun. 25, 2014, now U.S. Pat. No. 9,824,190, which claims the benefit of U.S. Provisional Application No. 61/839,528, filed Jun. 26, 2013, all of which are incorporated herein by reference in their entireties.

TECHNICAL FIELD

Various embodiments of the present disclosure relate generally to creating and selecting models for predicting medical conditions. More specifically, particular embodiments of the present disclosure relate to systems and methods for first creating a library of models that predict medical conditions. When new data from a patient is received, models may be selected from a library of models to predict medical conditions including adverse health events.

BACKGROUND

An important aspect of medical care is disease management. For effective disease management, it is not only important to understand the cause of any medical episodes related to the underlying medical conditions and taking suitable actions, but it is equally important to be able to predict any future episodes requiring medical intervention beforehand.

With the advent of sensors and health monitoring technologies that are user friendly, the collection of health and behavior data has increased significantly. However, prevailing methods fail to accurately predict future episodes requiring medical intervention.

For example, diabetes is a result of poor control over one's blood glucose (BG) levels. Two major forms of diabetes are type 1 and type 2. Type 1 occurs from the body's failure to produce insulin, and requires the person to inject insulin or wear an insulin pump. Type 2 is a result of body's resistance to insulin, a condition in which cells do not properly use insulin, sometimes combined with an absolute insulin deficiency.

One of the major complications of diabetes resulting in acute episodes is called hypoglycemia. An episode refers to when a person's BG level drops below approximately 70 mg/dL. Such an episode results in inadequate supply for glucose to the brain which may cause seizures, unconsciousness, mild dysphoria, and may even result in death if not treated immediately. Hypoglycemia may be caused by numerous factors including an insulin overdose, inadequate nutrition, lack of nutrition before exercise, natural metabolism, abnormal blood glucose values, amount of nutrition, and medication.

Hypoglycemia may be treated by restoring BG levels to normal by medication, nutrition or glucose tablets. Major factors causing hypoglycemia are overdosing of medications, inadequate nutrition, and lack of nutrition before exercise and due to one's metabolism. However, data related to such factors is often not available from patients. While prevailing techniques use continuous glucose monitoring devices (CGM) to immediately respond to such episodes. These techniques do not allow for accurate predictions of future hypoglycemic episodes based on patient-reported self-monitored blood glucose (SMBG) data.

SUMMARY OF THE DISCLOSURE

Embodiments disclose systems and methods for creating and selecting models for predicting medical conditions, specifically medical episodes requiring interventions.

According to some embodiments, computer-implemented methods are disclosed for selecting one or more models for predicting medical conditions. In an exemplary embodiment, the method includes receiving data related to a patient, extracting metadata from the received data, and selecting the one or more models from a library of models based on the extracted metadata. The method further includes applying the selected one or more models and generating a notification when the application of the selected one or more model indicates an intervention is necessary.

According to some embodiments, systems are disclosed for selecting one or more models for predicting medical conditions. One system includes a memory having processor-readable instructions stored therein and a processor configured to access the memory and execute the processor-readable instructions, which when executed by the processor configures the processor to perform a method. In an exemplary embodiment, the method includes receiving data related to a patient, extracting metadata from the received data, and selecting the one or more models from a library of models based on the extracted metadata. The method further includes applying the selected one or models and generating a notification when the application of the selected one or more model indicates an intervention is necessary.

According to some embodiments, a non-transitory computer readable medium is disclosed as storing instructions that, when executed by a computer, cause the computer to perform a method, the method includes receiving data related to a patient, extracting metadata from the received data, and selecting the one or more models from a library of models based on the extracted metadata. The method further includes applying the selected one or models and generating a notification when the application of the selected one or more model indicates an intervention is necessary.

According to some embodiments, the methods may further include receiving data related to the patient's blood glucose level, extracting metadata indicating whether the patient's blood glucose level is continuous glucose monitor data or self-monitored blood glucose data, selecting a first type of model when the extracted metadata indicates that the patient's blood glucose level is continuous glucose monitor data and selecting a second type of model when the extracted metadata indicates that the patient's blood glucose level is self-monitored blood glucose data. The method may further include selecting the second type of model when the extracted metadata indicates that the patient's blood glucose level is continuous glucose monitor data and self-monitored blood glucose data, and transmitting the generated notification to one or more user devices where Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

While the present disclosure is described herein with reference to illustrative embodiments for particular applications, it should be understood that embodiments of the present disclosure are not limited thereto. Other embodiments are possible, and modifications can be made to the described embodiments within the spirit and scope of the teachings herein, as they may be applied to the above-noted field of the present disclosure or to any additional fields in which such embodiments would be of significant utility.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In view of the challenges associated with the conventional techniques outlined above, systems and methods are disclosed herein for creating and selecting models for predicting medical conditions.

Reference will now be made in detail to the exemplary embodiments of the disclosure, examples of which are illustrated in the accompanying drawings. Wherever possible, the same reference numbers will be used throughout the drawings to refer to the same or like parts.

Figure 1:
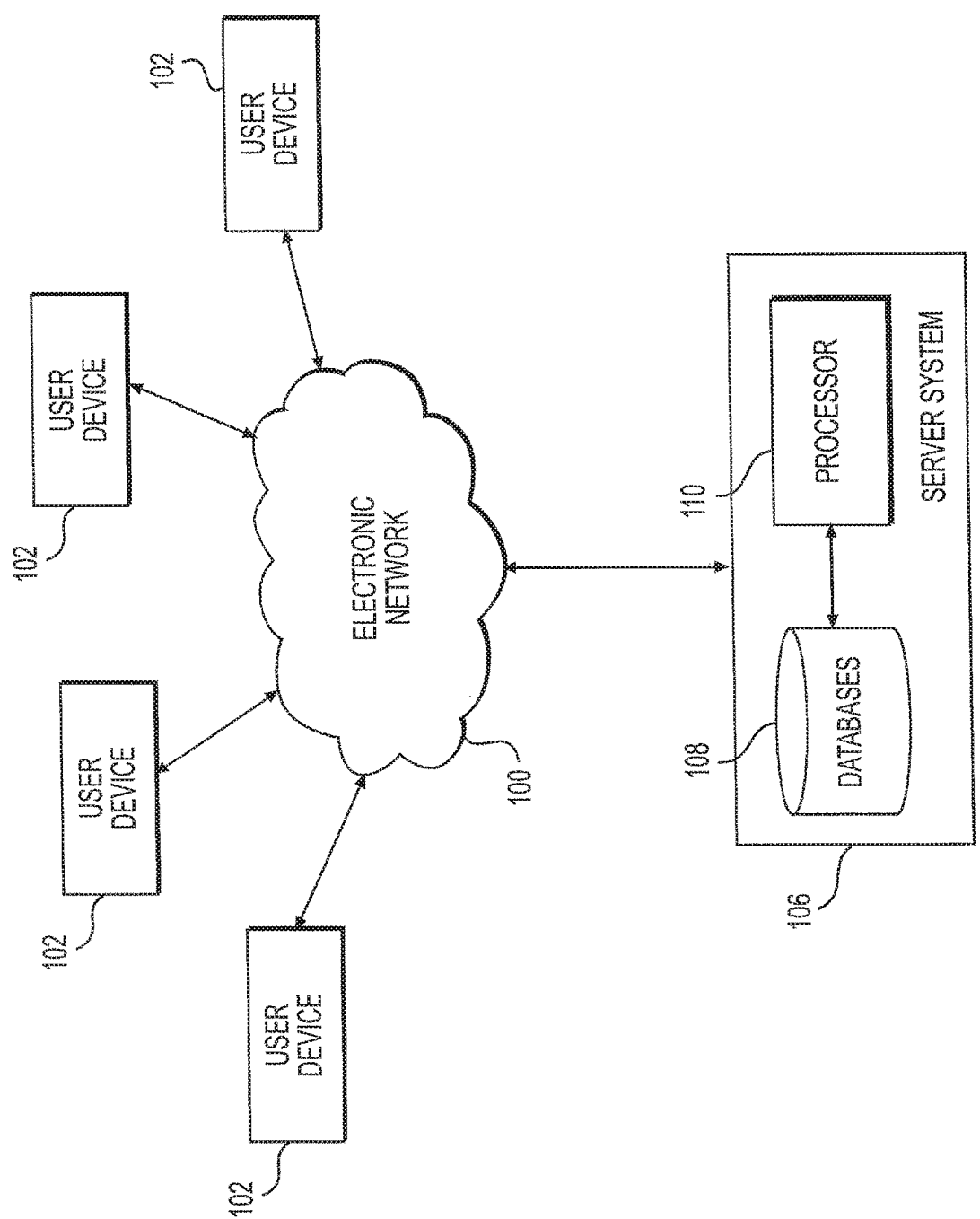
FIG. 1 is a schematic diagram of a network environment for selecting one or more models predicting medical conditions, according to an embodiment of the present disclosure.

FIG. 1 is a schematic diagram of an exemplary network environment in which various systems may select one or more models predicting medical conditions (including, but not limited to, adverse health events), according to an embodiment of the present disclosure. As shown in FIG. 1, the environment may include a plurality of user or client devices 102 that are communicatively coupled to each other as well as one or more server systems 106 via an electronic network 100. Electronic network 100 may include one or a combination of wired and/or wireless electronic networks. Network 100 also may include a local area network, a medium area network, or a wide area network, such as the Internet.

In one embodiment, each of user or client devices 102 may be any type of computing device configured to send and receive different types of content and data to and from various computing devices via network 100. Examples of such a computing device include, but are not limited to, mobile health devices, a desktop computer or workstation, a laptop computer, a mobile handset, a personal digital assistant (PDA), a cellular telephone, a network appliance, a camera, a smart phone, an enhanced general packet radio service (EGPRS) mobile phone, a media player, a navigation device, a game console, a set-top box, a biometric sensing device with communication capabilities, or any combination of these or other types of computing devices having at least one processor, a local memory, a display (e.g., a monitor or touchscreen display), one or more user input devices, and a network communication interface. The user input device(s) may include any type or combination of input/output devices, such as a keyboard, touchpad, mouse, touchscreen, camera, and/or microphone.

In one embodiment, each of the user or client devices 102 may be configured to execute a web browser, mobile browser, or additional software applications that allows for input from patients and other individuals from the medical field including physicians, nurses, pharmacists, etc. One or more of user or client devices 102 may be further configured to execute software allowing for monitoring of patient related data including the ability to receive user input or utilizing associated sensors to monitor patient conditions. For example, user or client devices 102 may contain an application which allows it to receive data from a paired and/or integrated blood sugar level monitor and then transmit the data to other entities within environment 100. Alternatively, user or client devices 102 may contain applications which allow for a patient to input information related to patient behavior such as consumption of nutrition and medication.

Server system 106 in turn may be configured to receive data related to one or more patients including data related to patients' health or medical condition, including information related to prescribed medication regimens, vitals, chronic diseases, nutritional requirements, nutrition consumption, medication consumptions, etc. It should be noted that while a singular server system 106 is described, method 200, described below with respect to FIG. 2, may be implemented using a plurality of server systems working in combination, a single server device, or a single system.

Also, as shown in FIG. 1, server system 106 may include one or more databases 108. In an embodiment, databases 108 may be any type of data store or recording medium that may be used to store any type of data. For example, databases 108 may store data received by or processed by server system 106 including information related to a patient and or a library of models which aid in predicting medical conditions.

Additionally, as shown in the example of FIG. 1, server system 106 may include processor 110. In an embodiment, processor 110 may be configured to execute a process for creating and selecting models for predicting medical conditions. The management process may, for example, continue to receive patient data, generate models utilizing data related to patients, and then select models for predicting medical conditions.

Figure 2:
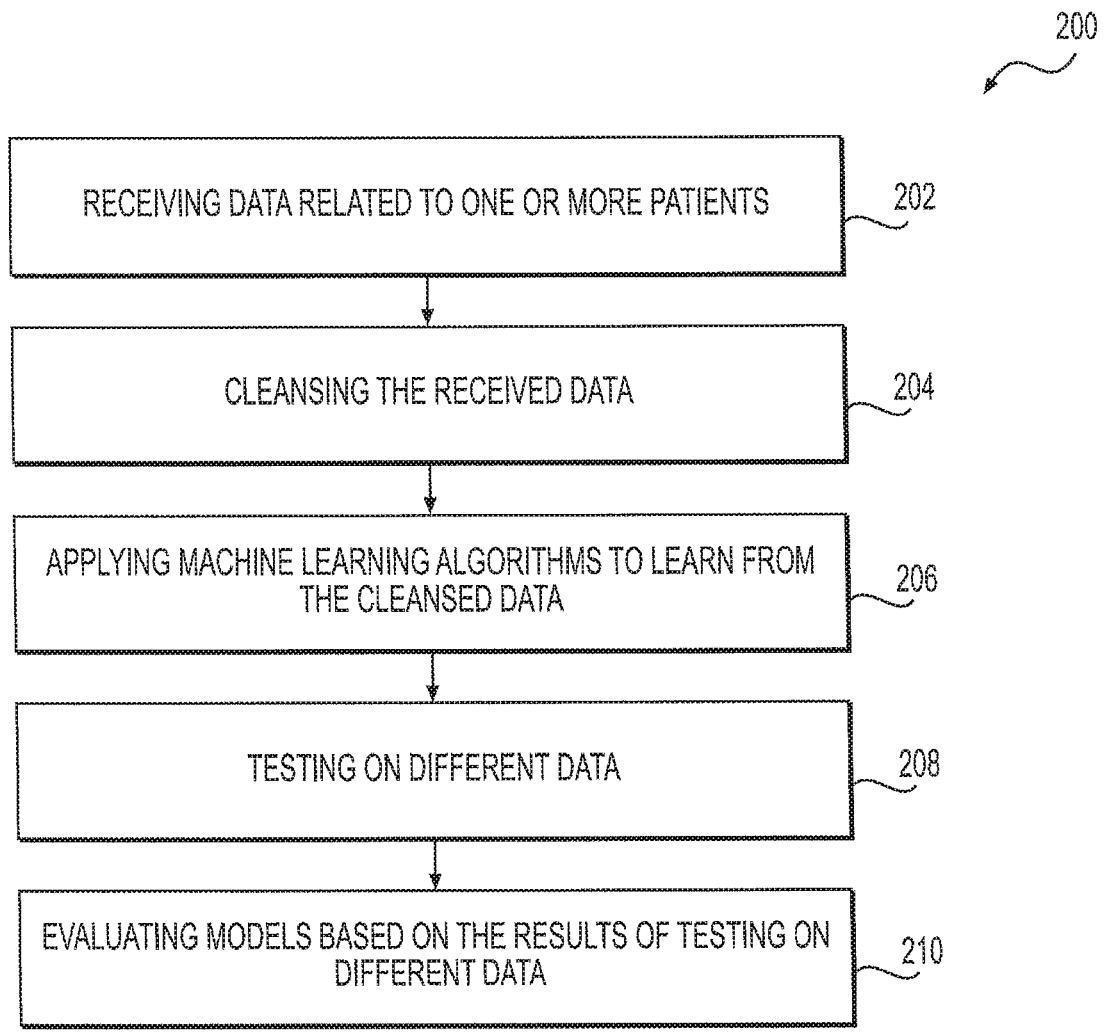
FIG. 2 is a flow diagram of an exemplary method 200 for creating one or more models, according to an embodiment of the present disclosure.

In an embodiment, processor 110 may be configured to receive instructions and data from various sources including user or client devices 102 and store the received data within databases 108. In some implementations, any received data may be stored in the databases 108 in an encrypted form to increase security of the data against unauthorized access and complying with HIPAA privacy regulations. Processor 110 or any additional processors within server system 106 also may be configured to provide content to client or user devices 102 for display. For example, processor 110 may transmit displayable content including messages or graphic user interfaces soliciting information related to patient behavior. Additionally, the messages may indicate that an intervention is necessary due to a predicted medical condition A first aspect of the exemplary method 200 entails creating a library with models which can predict medical occurrences. Specifically, FIG. 2 is a flow diagram of an exemplary method 200 for creating one or more models for predicting medical conditions, according to an embodiment of the present disclosure In step 202, method 200 includes receiving data related to one or more patients. The received data may include receiving data related to patients' health or medical conditions, including information related to prescribed medication regimens, vitals, chronic diseases, nutritional requirements, nutrition consumption, medication consumptions, etc. For example, for patients dealing with hypoglycemia, the received data may include information related to a patient's blood glucose level, amounts of nutrition consumed, time of the day associated with checking blood glucose levels and consumption of nutrition and times associated with a patient's medical regimen.

In embodiments, the data may be received based on self-reporting by patients. Alternatively, devices such as continuous glucose monitoring devices (CGM) or self-monitoring of blood glucose devices (SMBG) may transmit this data to server 106 automatically. In embodiments, SMBG data may have certain advantages over CGM data including more accuracy even if it is significantly sparser than CGM data. The more accurate SMBG data may be more readily available from devices configured to automatically upload patient data to servers 106.

In step 204, method 200 may include cleansing the received data. In detail, raw data is transformed into a form that is easily readable without ambiguity for a machine learning algorithm. In embodiments, the cleansing involves determining the presence of anomalies, errors, missing values, and large number ranges etc. in the received data and fixing them. The cleansing may be conducted by an automated process defined by rules replicating manual data cleansing by a data analyst. In other embodiments, a data analyst may input instructions for manually cleansing the received data.

In embodiments, cleansing the received data allows machine learning algorithms to more readily understand underlying patterns in the data. To minimize the introduction of manual bias based on modifying the original pattern in raw data, missing value instances may be replaced with indicators such as 'N/A' or '0'. In embodiments, this may help the machine learning algorithm in understanding that a value should have existed in that location and while the value may be ignored, the fact that such a value existed may be considered during its learning process.

In some embodiments, cleansing the data may refer to using only some parts of the received data or transforming the received data. For example, for diabetes patients, the only relevant aspects of data for providing to machine learning algorithms may be the blood glucose levels and the associated time stamps. In such a scenario, the rest of received data related to the patient may be removed from consideration. In some embodiments, the time stamp may be used to calculate other variable such as time of the day, date, month, etc. Additionally, duration between successive values of blood glucose levels may be determined.

In step 206, method 200 includes applying machine learning algorithms to learn from the cleansed data. In instances, a certain percentage of data points may be utilized as a training set for the machine learning algorithm. For example, out of a total 1000 data points by 100 patients, 500 data points may be used for training/learning while the rest of the 500 data points may be used for testing.

In embodiments, machine learning algorithms learn all possible patterns within the patient data points. The machine learning algorithms may further learn about patterns between additional factors as well as the relationship of those patterns with a prediction variable. The prediction variable is the variable that is to be predicted utilizing the machine learning algorithms. Every algorithm has parametric values that define a configuration of the algorithm that best predicts the prediction variable. Such configurations are called models.

In step 208, method 200 includes testing on different data. Continuing the example from before, the 500 data points for testing may be applied to a model. The machine learning algorithms predict a prediction variable with a level of confidence. The level of confidence may indicate how accurate the prediction variable may be. In embodiments, to determine effectiveness of the models, the models need to be tested with various different data sets.

In embodiments, machine learning algorithms, include, but are not limited to support vector machines, k-nearest neighbor, Bayesian statistics (e.g., native Bayes), multi-layer perceptron's, and multivariate regressions.

In step 210, method 200 includes evaluating models based on the results of testing on different data of step 208. The prediction variable values that are removed before testing may be used as a reference. The values predicted by the model during testing may then be matched with the reference values to identify cases of data when the model did and did not predict correctly. The evaluation of whether the model led to an accurate prediction or not may be expressed in percentages. A model's success and failure in prediction may be expressed in the form of a table called a confusion matrix. For example, a confusion matrix may include values predicted by using a model and the actual (reference) value. These values may be utilized to determine a precision percentage which may also be included in the confusion matrix.

A model or plurality of models may be stored in a library of models (not illustrated) in databases 108. The models in the library of models may then be utilized by processor 110 to predict a need for medical intervention when new patient data is received.

As an example of a use case, consistent with embodiments of the present disclosure, 1000 blood glucose data points and respective timestamps may be received or stored (in databases 108) related to a 100 patients. The 1000 data points may be then split in half (or any suitable function), where 500 may be used for training the algorithm and the other 500 may be used for testing the models. If it is known that 250 of 500 data points utilized in testing are hypoglycemia events and a model predicts all of the 250 instances accurately, than the model is 100% accurate.

In such a scenario, with an exemplary model with 100% accuracy, when a patient provides 20 new blood glucose data points, application of the model may accurately predict if the patient may encounter a hypoglycemic event the next day and if so at what time of the day. If a hypoglycemic event is predicted for the next day, this information may be used to generate a notification that medical intervention may be necessary. For example, the notification may inform a system (not illustrated) controlling a patient's insulin pump to regulate an appropriate amount of insulin at the right time before the occurrence of the predicted event.

Further details regarding assessing performance of machine learning algorithms and selecting models are provided accordingly to exemplary embodiments. An important aspect in utilizing an appropriate machine learning algorithm is the interplay between bias, variance and model complexity.

A first aspect of the process is determining a quantitative response. For example, there may be a target variable Y, a vector of inputs X, and a prediction model $\hat{f}(X)$ that has been estimated from a training set T.

The loss function for measuring errors between Y and $\hat{f}(X)$ may be denoted by $L(Y, \hat{f}(X))$, where:

$$L(Y,\hat{f}(X))=((Y-\hat{f}(X))2 \text{ squared error} \quad (1.1)$$

$$L(Y,\hat{f}(X))=((Y-\hat{f}(X)) \text{ absolute error}$$

Test error, also referred to as generalization error, may be the prediction error over an independent test sample:

$$\text{Err}T=E[L(Y,\hat{f}(X))|T] \quad (1.2)$$

Where both X and Y are drawn randomly from their joint distribution (population). Here the training set T is fixed, and test error refers to the error for this specific training set. A related quantity is the expected prediction error (or expected test error):

$$\text{Err}=E[L(Y,\hat{f}(X))]=E[\text{Err}T]. \quad (1.3)$$

Note that this expectation averages over everything that is random, including the randomness in the training set that produced $\hat{f}$.

Training error is the average loss over the training sample:

$$\text{Err}=(1/N)\Sigma\text{err}Ni=1 \, L(yi,\hat{f}(xi)). \quad (1.4)$$

It may be helpful to determine the expected test error of the estimated model $\hat{f}$. As the model becomes more and more complex, it may use the training data more and may be able to adapt to more complicated underlying structures. Hence, there is a decrease in bias but an increase in variance. Accordingly, there may be provided intermediate model complexity that provides minimum expected test error.

Unfortunately training error may not be a good estimate of the test error. Training error consistently decreases with model complexity, typically dropping to zero when the model complexity is increased enough. However, model with zero training error may be overfit to the training data and will typically generalize poorly.

To continue the hypoglycemia example, in the case of hypoglycemia prediction there may be a nominal/categorical response. Similarly, for a qualitative or categorical response G taking one of 2 values in a set G, labeled for convenience as k=0,1 (hypoglycemia YES/NO). Probabilities pk (X)=Pr (G=k|X) may be modeled, where the loss functions are:

$$L(G, G^{\wedge}(X)) = I(G \neq G^{\wedge}(X)) \, (0-1 \text{ loss}), \quad (1.5)$$

$$L(G, p^{\wedge}(X)) = -2\sum 2i = 1 \, I(G = k)\log p^{\wedge}k(X)$$

$$= -2\log p^{\wedge}G(X) \, (-2 \times \log - \text{likelihood}). \quad (1.6)$$

The quantity −2×the log-likelihood may be referred to as the deviance.

Again, test error here may be $\text{Err}T=E[L(G, G^{\wedge}(X))|T]$, the population mis-classification error of the classifier trained on T, and Err may be the expected misclassification error of not predicting hypoglycemia.

Training error may be the sample analogue, for example, $$\text{err}=(2/N)\Sigma Ni=1 \, \log p^{\wedge}gi(xi), \quad (1.7)$$

which is the sample log-likelihood for the model.

In embodiments, models may have a tuning parameter or parameters α where the prediction may be written as $\hat{f}\alpha(x)$. The tuning parameter may vary the complexity of a model and it is imperative to minimize error. This may include two aspects including estimating the performance of different models in order to choose the best one and estimating a model's prediction error (generalization error) on new data.

While method 200 is described as splitting the total data points into two sets to use as learning data and testing data, in some embodiments, the data points may be divided into three sets: a training set, a validation set, and a test set. The training set may be used to fit the models, the validation set may be used to estimate prediction error for model selection, and the test set may be used for assessment of the generalization error of the final chosen model. Ideally, the test set may be only used for data analysis. That is, if a first test-set is used repeatedly with various models, then the model with the model with smallest test-set errors may be chosen. Then the test set error of the final chosen model may underestimate the true test error, sometimes substantially because of its reliance on only the first test-set. In some additional embodiments, the data points may be divided in four or more sets as well.

In embodiments, an assessment of generalization performance of a learning method is very importance since it guides the choice of learning method or model that is selected. Additionally, the assessment provides a measure of the quality of the chosen model.

While FIG. 2 describes an exemplary method for creating one or more models. Additional methods may be utilized for creating the library of models consistent with exemplary embodiments. Furthermore, exemplary method 300 described below does not require that the library of models be necessarily created using exemplary method 200.

Figure 3:
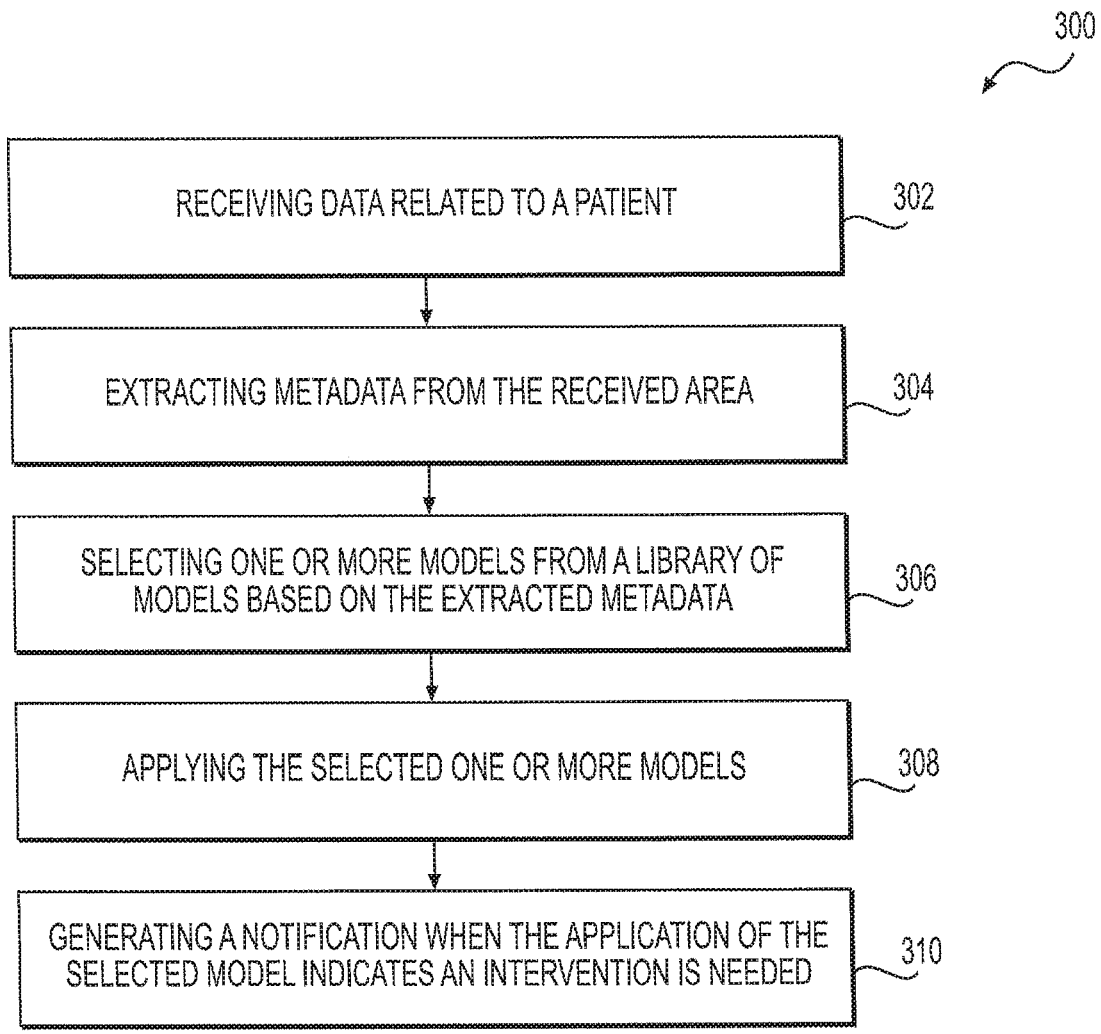
FIG. 3 is a flow diagram of a method 300 for selecting one or more models predicting medical conditions, according to an embodiment of the present disclosure.

FIG. 3 is a flow diagram of a method 300 for selecting one or more models predicting medical conditions including adverse health events, according to an embodiment of the present disclosure.

In step 302, method 300 includes receiving data related to a patient. For example, this data may be received and/or retrieved by processor 110 from one or more databases 108 or may be directly received from one or more user or client devices 102. The data may include clinical, behavioral, personal and system data. For example, self-reported data, data from one or more sensors (such as blood glucose testing machines), patient data from historical electronic records, secondary sources of data, system logs, and system-reported data that is based on inference or machine learning, etc.

In embodiments, self-reported data may include data that is provided by a user, for example, blood glucose levels and associated time stamps self-reported by the patient (SMBG) using one of client or user devices 102.

In embodiments, one or more sensors may include sensors related to patient's medical conditions or other related sensors. For example, blood glucose levels may be monitored from continuous glucose monitoring (CGM) devices for hypoglycemic patients. Similarly, pulmonary patients may have oxygen level monitors, etc. Additional sensors may provide information such as location information from mobile devices, weather information from publicly available data sources, elevation information, etc.

In embodiments, secondary sources of data may include information related to a patient that may be provided by other individuals or entities such as caregivers. This data may include subjective observations regarding patient behavior and moods. Additionally, system logs such as data from mobile applications may be utilized. The systems logs may provide information including when a first health monitoring application started being used by a patient, how it has been used over a certain time period, etc. As another example, an exercise monitoring application may provide data related to a patient's exercise.

System-reported data that is based on inference or machine learning may include utilizing data related to certain conditions and determining that other conditions may exist based on machine learning. For example, low levels of exercise and certain vital signs may indicate the possibility of depression or a probability of a depressive episode.

This received data may previously be generated utilizing processor 110 and stored in databases 108. Alternatively, the received data may be transmitted by one of user or client devices 102, including data previously transmitted and stored in databases 108. In embodiments, one of user or client devise 102 may transmit data in real time, continuously, periodically, or based on a predetermined duty cycle.

In step 304, method 300 includes extracting metadata from the received data. In detail, metadata may be extracted from the received data to extract information about data such as descriptive statistics, availability, data type, category type, degree of relationship and/or influence.

In embodiments, descriptive statistics may include mean, standard deviation, variance, etc. of the objective data that is received. Objective data may include numerical values related to vital signs, nutrition consumed, and medication consumed, etc.

Availability may refer to determining when different types of data is available. For example, certain days SMBG data may have been input by a hypoglycemic patient and therefore may be available. For those instances, frequency information may also be extracted. Frequency information allows for picking of models which are more efficient for the amount of data that is available. For other days, CGM data may be available and that data is utilized. As an additional example of different types of data, the different types of data may be low-frequency data (such as data from a lab setting) as opposed to high-frequency data (such as captured by home monitoring devices.)

Data type may refer to the types of data that is received. For example, the received data may related to conditions external to the patient such as location and weather. Accordingly, this extracted metadata may allow for selection of appropriate location specific models or weather-specific models. The selection process is explained in further detail below with respect to the explanation of step 306.

Category type may refer to whether the received data is clinical, behavioral, or personal. Clinical data may include data that is captured in a clinical setting including a visit to a doctor's office or results from a medical lab. Behavioral data may include data related to a patient's behavior such as sleeping, exercising, eating, patient's mood, and consuming medications, etc. Personal data may include, but is not limited to, data related to the patient including weight, height, body fat, vital signs, and medical history, etc.

Degree of relationships and/or influence on other categories may refer to contextualization of received data. In an embodiment, if a certain category is selected, then there may be an assigned value to a related category. For example, data related to a person's weight may be received but if such an increase correlates with an increase in a blood pressure level, a value may be assigned to the blood pressure level even though no data is received directly providing a blood pressure level.

In embodiments, metadata may be extracted based on categories of stored library of models. Alternatively, the received data may be processed for extraction using batch-based data or streaming data. For example, rules engines or a XML parser may be used for extracting the metadata from the received data.

In step 306, method 300 may include selecting one or more models from a library of models based on the extracted metadata. For example, processor 110 may apply rules using the extracted metadata to determine the one or more models to select from a library of models that are generated by method 200 described above. The rules may be simple logical, mathematical, algorithmic rules, or machine learned models. These rules may be applied to models that are stored in databases 108. In embodiments, a library of models may be referred to as logical library (LL). Models may be stored in the logical library (LL) independently and/or may be categorized per one or more criteria. For example, the categories may be clinical, behavioral, or personal data. However, other suitable categorization may be applied.

In additional embodiments, a plurality of models or a combination of models are to be selected. In instances when more than one combination exists for a given context, potential conflicts may be resolved by following certain rules of selection. For example, rules of selection may provide limitations for picking rules and/or models. The rules may include limitations regarding allowable and non-allowable combinations of models. The rules also may prioritize a list of eligible models or rules that may be applied. In embodiments, a threshold number of highly prioritized models may be selected. The rules of selection also may be based on randomized logic. The rules may be specific or agnostic of a given user or population.

In step 308, method 300 may include applying the selected one or more models. For example, the selected models may be applied to received data or the extracted metadata to predict medical occurrences. An exemplary use case is described below with respect to FIG. 4 providing further insight into this step.

In step 310, method 200 may include generating a notification when the application of the selected model indicates an intervention may be needed. For example, for a hypoglycemia patient, when it appears that a patient's blood glucose level will likely drop based on application of the model, a notification may be generated. The generated notification may be provided to the patient or other concerned entities such as pharmacists, physicians, and clinicians, etc. The notifications may serve as reminders as well as instruments to force interventions. For example, a prediction of a critical medical condition may trigger an emergency call from the physician's office to the patient. If the patient is not responsive, the medical service provider may contact a patient's emergency contact person and/or local emergency medical services entities.

In some embodiments, a motivation may trigger a clinical or behavioral action such as medication dosage change or motivational messaging. Additionally, a patient may receive information regarding correcting actions that may be taken to reduce the probability of experiencing an adverse health event. Therefore, a patient may take a corrective action such as changing their diet, resting, or consuming a medication to aid in preventing or reducing the probability of an adverse health event.

In some embodiments, the metadata does not need to be extracted. In such a scenario, rules may be stored in databases 108 that allow for one or more models to be selected from the library of models based on the received data.

Figure 4:
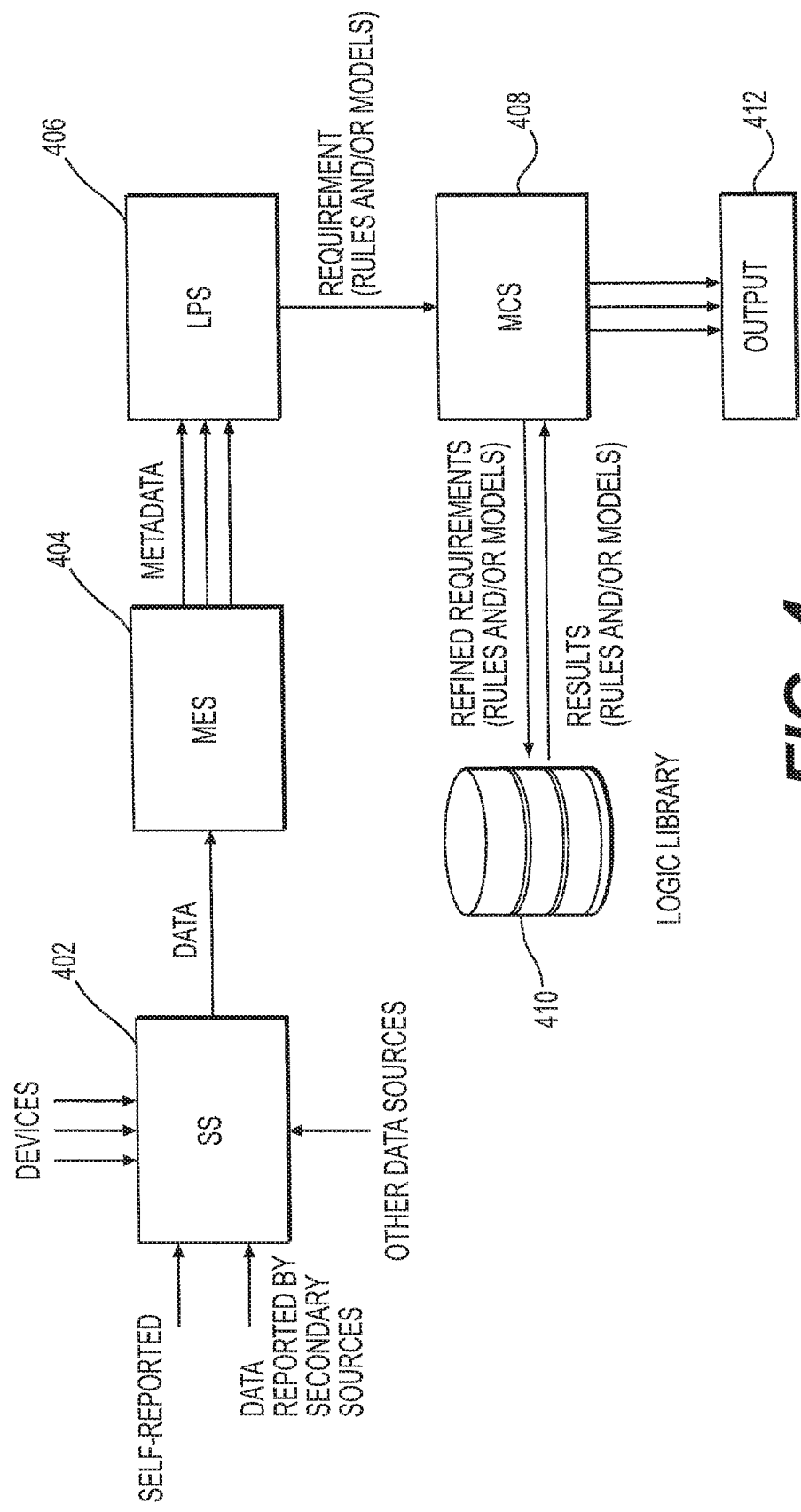
FIG. 4 illustrates an exemplary use case applying the principles of a method, according to an embodiment of the present disclosure.

FIG. 4 presents an exemplary use case applying the principles of method 300 presented in FIG. 3 above, according to an embodiment of the present disclosure. One of ordinary skill in the art would comprehend that the boxes 402-410 illustrated in FIG. 4 do not represent structural limitations. Rather, boxes 402-410 represent possible implementations of combinations of one or more of the steps of method 300 that are executed by processor 110.

This use cases deals with a prediction of whether a patient may slip in to a coma (a prolonged state of unconsciousness) within a given calendar week. A data storage/stream service (SS) 402 may store and/or receive data related to the patient. For example, the stored data may include information related to a patient including the fact that the patient has Type 2 diabetes and has been diagnosed with severe depression. This information may have been previously received and stored within databases 108 as being associated with the patient. Additional received data by SS 402 may include self-reported data such as blood glucose levels and associated time stamps self-reported by the patient (SMBG). Additionally, information from one or more sensors may be received such as blood glucose levels from a continuous glucose monitoring (CGM) device. Furthermore, information received from one or more sensors may include location information from mobile devices or weather information from publicly available data sources. Additionally, information may include secondary sources of data, such as information provided by caregivers. For example, with regards to depression for this exemplary use case, the patient may provide the primary data regarding their symptoms while the caregiver may provide secondary data including observations regarding the patient.

The received data may be provided to metadata extractor service (MES) 404 for extracting metadata from the data received by SS 402. MES 404 may extract metadata from the received data. For example, for days when SMBG is available, MES 404 may extract frequency information and specifies that the received data is sparsely distributed. However, for days when CGM data is available, MES 404 may specify that the received data is densely distributed.

MES 404 may then send the extracted metadata information to logic processing service (LPS) 406. LPS 406 may use the metadata information to decide which models to pick based on pre-defined rules. For example, LPS 406 may choose to pick SMBG-specific model for cases when SMBG data is available. Additional examples of rules regarding picking models may include LPS 406 taking numerous additional factors into consideration for picking the appropriate model(s) including data reported by patient versus those reported by a caregiver, location-specific models based on location information from mobile device, and weather-specific models based on received weather information.

While in many instances, output of LPS 406 may be sufficient to select the models, it may be important to check if there are any conflicts between selecting multiple models and if there are combinations of models that may be chosen. In this example, since the patient has two diseases of diabetes and depression, the chosen models must be applicable for both without any major issues. It is possible that the symptoms reported by patient may conflict with the information reported by the caregiver. Accordingly, in this exemplary use case, model combinator service (MCS) 408 may be utilized to solve such a possible conflict by providing predefined rules to prioritize patient provided data over date supplied by, e.g., a caregiver, or vice-versa depending on context.

In embodiments, to select the correct models based on the requirements from MCS 408, LL 410 may be queried and models applicable for both diseases and models that take weather, location, and symptoms, or any other suitable factors, into account, may be retrieved and provided as output 412.

The output 412 may be utilized to generate notifications when a medical intervention may be necessary. In this instance, if it appears that the patient may go into coma, a notification may be generated. This notification may be provided to the patient, caregiver, physician, physician's assistant, etc. For example, a diabetes patient may get a notification that unless they inject insulin immediately, they are at risk for an hypoglycemic episode.

In embodiments, exemplary systems consistent with the present disclosure may be designed to perform automatic self-maintenance and tuning with regards to the various models. For example, the exemplary systems may be able to identify errors and modify rules associated with selection of models to minimize error over time. Additionally, new possible models may be automatically evaluated and considered to be added to the pool of models for selection. Furthermore, machine learning algorithms may be used for learning about new types of data that may be received and recommend possible model selection logic for its predictions, based on performance of such models on similar data.

In embodiments, stochastic models may be utilized. However, their results may be transformed into probabilistic and/or deterministic terms. For example, all of the data first may be transformed into deterministic data. The transformation may occur based on inputs by a data analyst, a particular set of rules defining the transformation, or a machine learned algorithm. Once, all the data has been transformed into deterministic data, all the data may be combined since it is in the same format. Using deterministic data allows experts trained in the field to specify the rules for selection of models in an easier manner.

The examples described above with respect to FIGS. 1-4, or any part(s) or function(s) thereof, may be implemented using hardware, software modules, firmware, tangible computer readable media having instructions stored thereon, or a combination thereof and may be implemented in one or more computer systems or other processing systems.

In embodiments, being able to predict an occurrence of an adverse medical event, such as a hypoglycemic event may have many benefits. For example, a pay/self-insured employer may be interested in screening patients who have high risk of hypoglycemia within a forecasted period in order to adjust premium cost of health insurance or provide for additional care. Alternatively, a hospital may be interested in identifying high-risk patient to prevent instances of readmission. Similarly, an insurance payer may use predictions to aid in preventing expensive emergency room visits. Additionally, guidance, including in the form of messages and suggestions, may be provided to a patient based on the predictions including suggestions to diet, medication regimen, or nutrition, etc.

Figure 5:
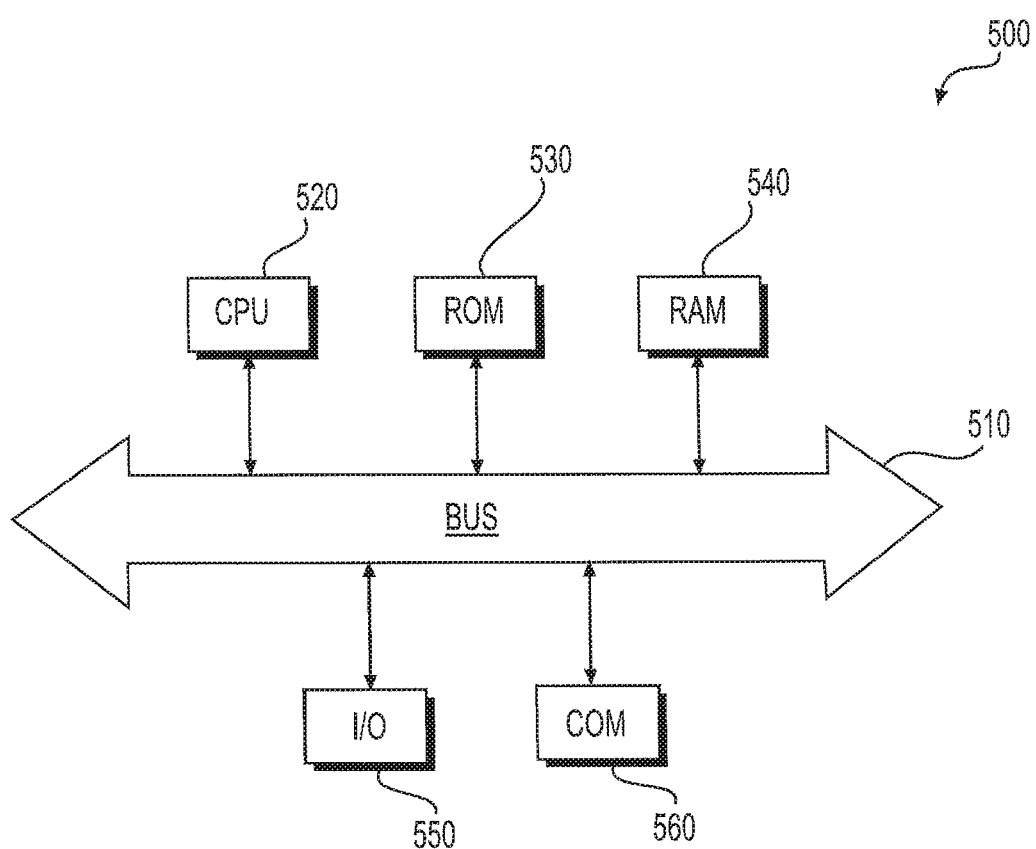
FIG. 5 is a block diagram of an exemplary computer system in which embodiments of the present disclosure may be implemented.

FIG. 5 illustrates a high-level functional block diagram of an exemplary computer system 500, in which embodiments of the present disclosure, or portions thereof, may be implemented, e.g., as computer-readable code. For example, each of the exemplary devices and systems described above with respect to FIG. 1 can be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIG. 1, as described above.

If programmable logic is used, such logic may be executed on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, at least one processor device and a memory may be used to implement the above-described embodiments. A processor device may be a single processor, a plurality of processors, or combinations thereof. Processor devices may have one or more processor "cores."

Various embodiments of the present disclosure, as described above in the examples of FIGS. 1-4, may be implemented using computer system 500. After reading this description, it will become apparent to a person skilled in the relevant art how to implement embodiments of the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

As shown in FIG. 5, computer system 500 includes a central processing unit (CPU) 520. CPU 520 may be any type of processor device including, for example, any type of special purpose or a general-purpose microprocessor device. As will be appreciated by persons skilled in the relevant art, CPU 520 also may be a single processor in a multi-core/multiprocessor system, such system operating alone, or in a cluster of computing devices operating in a cluster or server farm. CPU 520 may be connected to a data communication infrastructure 610, for example, a bus, message queue, network, or multi-core message-passing scheme.

Computer system 500 also may include a main memory 540, for example, random access memory (RAM), and also may include a secondary memory 530. Secondary memory 530, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc. which is read by and written to by the removable storage drive. As will be appreciated by persons skilled in the relevant art, such a removable storage unit generally includes a computer usable storage medium having stored therein computer software and/or data.

In alternative implementations, secondary memory 530 may include other similar means for allowing computer programs or other instructions to be loaded into computer system 500. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to computer system 500.

Computer system 500 also may include a communications interface ("COM") 560. Communications interface 560 allows software and data to be transferred between computer system 500 and external devices. Communications interface 660 may include a modem, a network interface (such as an Ethernet card), a communications port, a PCM-CIA slot and card, or the like. Software and data transferred via communications interface 560 may be in the form of signals, which may be electronic, electromagnetic, optical, or other signals capable of being received by communications interface 560. These signals may be provided to communications interface 560 via a communications path of computer system 600, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Computer system 500 also may include input and output ports 550 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It would also be apparent to one of skill in the relevant art that the present disclosure, as described herein, can be implemented in many different embodiments of software, hardware, firmware, and/or the entities illustrated in the figures. Any actual software code with the specialized control of hardware to implement embodiments is not limiting of the detailed description. Thus, the operational behavior of embodiments will be described with the understanding that modifications and variations of the embodiments are possible, given the level of detail presented herein.

It is to be understood that both the foregoing general description and the following detailed description are exemplary and explanatory only and are not restrictive of the disclosed embodiments, as claimed.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for selecting one or more models for predicting medical conditions, the method comprising:
    receiving, using a processor, initial data related to a user, wherein receiving the initial data includes receiving at least some initial data, wirelessly over a server, from a first device, and includes receiving at least some initial data that is self-monitored;
    processing, using the processor and one or more machine learning algorithms, the initial data to identify patterns between the initial data, and other data related to the user's medical condition;
    assigning values to an unmeasured data category for which no measured data is received by the processor, and processing the unmeasured data category, using the processor and the one or more machine algorithms, to identify one or more patterns between the values of the unmeasured data category, the initial data, and the other data,
    creating a library of models containing a plurality of models based on the identified patterns;
    after creating the library of models, receiving additional data related to the user, wherein receiving additional data includes receiving at least some additional data, wirelessly over a server, from a first device, and includes receiving at least some additional data that is self-monitored;
    extracting metadata from at least some of the received additional data, wherein extracting metadata from at least some of the received additional data comprises extracting metadata indicating whether a given stream of data is from a first device or is self-monitored;
    selecting the one or more models from the library of models based on the extracted metadata, wherein selecting the one or more models from the library of models based on the extracted metadata comprises selecting a first type of model when the extracted metadata indicates that the data is from a first device, selecting a second type of model when the extracted metadata indicates that the data is self-monitored, and selecting the second type of model when the extracted metadata indicates that the data includes both data from a first device and self-monitored data;
    applying the selected one or models; and
    generating a notification when the application of the selected one or more models indicates an intervention is necessary.

2. The computer-implemented method of claim 1, further comprising:
    transmitting the generated notification to one or more user devices.

3. The computer-implemented method of claim 1, wherein the notification includes corrective actions to be taken by the user to change a diet of the user.

4. The computer-implemented method of claim 1, wherein the one or more machine learning algorithms include one or more of support vector machines, k-nearest neighbor, Bayesian statistics, multi-layer perceptrons, and multivariate regressions.

5. The computer-implemented method of claim 1, further including predicting an occurrence of a medical event, and a time at which the medical event will occur, wherein the intervention includes one or more actions for the user to take to prevent occurrence of the medical event.

6. The computer-implemented method of claim 1, wherein the intervention includes sending a control signal to an insulin pump of the user to regulate an amount of insulin administered to the user.

7. The computer implemented method of claim 1, wherein assigning values to the unmeasured data category is based on data received by the processor.

8. The computer-implemented method of claim 1, further including receiving a weight of the user, wherein the unmeasured data category is blood pressure of the user, the processor does not receive any blood pressure data, and values are assigned to the blood pressure of the user based on the weight of the user.

9. The computer-implemented method of claim 1, wherein the initial data includes one or more of blood glucose levels of the user, nutrition consumed by the user, times of day associated with checking the blood glucose levels of the user, times of day associated with the nutrition consumed by the user, sleep of the user, exercise performed by the user, medication consumed by the user, and mood of the user, and the method further includes processing, using one or more machine learning algorithms, the initial data to identify patterns between the blood glucose levels of the user, and the one or more of nutrition consumed by the user, times of day associated with checking the blood glucose levels of the user, times of day associated with the nutrition consumed by the user, sleep of the user, exercise performed by the user, medication consumed by the user, and mood of the user.

10. The computer-implemented method of claim 1, wherein the initial data includes each of blood glucose levels of the user, nutrition consumed by the user, times of day associated with checking the blood glucose levels of the user, times of day associated with the nutrition consumed by the user, sleep of the user, exercise performed by the user, medication consumed by the user, and mood of the user, and the method further includes processing, using one or more machine learning algorithms, the initial data to identify patterns between each of the blood glucose levels of the user, and the one or more of nutrition consumed by the user, times of day associated with checking the blood glucose levels of the user, times of day associated with the nutrition consumed by the user, sleep of the user, exercise performed by the user, medication consumed by the user, and mood of the user.

11. A system for selecting one or more models for predicting medical conditions, the system comprising:
    a memory having processor-readable instructions stored therein; and
    a processor configured to access the memory and execute the processor-readable instructions, which, when executed by the processor configures the processor to perform a method, the method comprising:

receiving initial data related to a user, wherein receiving the initial data includes receiving at least some initial data, wirelessly over a server, from a first device, and includes receiving at least some initial data that is self-monitored;

assigning values to a first data category for which no measured data is received by the processor;

processing, using one or more machine learning algorithms, the initial data to identify patterns between the initial data, and other data related to the user's medical condition;

creating a library of models containing a plurality of models based on the identified patterns;

after creating the library of models, receiving additional data related to the user, wherein receiving additional data includes receiving at least some additional data, wirelessly over a server, from a first device, and includes receiving at least some additional data that is self-monitored;

extracting metadata from at least some of the received additional data, wherein extracting metadata from at least some of the received additional data comprises extracting metadata indicating whether a given stream of data is from a first device or is self-monitored;

selecting the one or more models from the library of models based on the extracted metadata, wherein selecting the one or more models from the library of models based on the extracted metadata comprises selecting a first type of model when the extracted metadata indicates that the data is from a first device, and selecting a second type of model when the extracted metadata indicates that the data is self-monitored;

applying the selected one or models; and generating a notification when the application of the selected one or more model indicates an intervention is necessary.

12. The system of claim 11, wherein the method further comprises:
transmitting the generated notification to one or more user devices.

13. The system of claim 12, wherein the generated notification contains one or more intervention options.

14. The system of claim 11, wherein assigning values to the first data category is based on data received by the processor.

15. The system of claim 11, further including receiving a weight of the user, wherein the first data category is blood pressure of the user, the processor does not receive any blood pressure data, and values are assigned to the blood pressure of the user based on the weight of the user.

16. A non-transitory computer-readable medium storing instructions, the instructions, when executed by a computer system cause the computer system to perform a method, the method comprising:

receiving initial data related to a user, wherein receiving the initial data includes receiving at least some initial data, wirelessly over a server, measured from two different types of devices;

extracting metadata from the received initial data to determine which of the two different types of devices was used to measure the initial data;

processing, using one or more machine learning algorithms, the initial data to identify patterns between the initial data, and other data related to the user's medical condition;

creating a library of models containing a plurality of models based on the identified patterns;

after creating the library of models, receiving additional data related to the user, wherein receiving additional data includes receiving at least some additional data, wirelessly over a server, from each of the two different types of devices;

selecting the one or more models from the library of models based on the extracted metadata, wherein selecting the one or more models from the library of models based on the extracted metadata comprises selecting a first type of model when the extracted metadata indicates that the data was measured from a first type of the two different types of devices, and selecting a second type of model when the extracted metadata indicates that the data was measured from a second type of the two different types of devices;

applying the selected one or models; and generating a notification when the application of the selected one or more model indicates an intervention is necessary.

17. The non-transitory computer readable medium of claim 16, wherein the two types of devices includes a continuous glucose monitoring device, and a device for collecting self-monitored blood glucose data.

18. The non-transitory computer readable medium of claim 16, further comprising assigning values to a first data category for which no measured data is received by the processor, wherein assigning values to the first data category is based on data received by the processor.

19. The non-transitory computer readable medium of claim 16, further including receiving a weight of the user, wherein the first data category is blood pressure of the user, the processor does not receive any blood pressure data, and values are assigned to the blood pressure of the user based on the weight of the user.

20. The non-transitory computer readable medium of claim 16, wherein the initial data includes one or more of blood glucose levels of the user, nutrition consumed by the user, times of day associated with checking the blood glucose levels of the user, times of day associated with the nutrition consumed by the user, sleep of the user, exercise performed by the user, medication consumed by the user, and mood of the user, and the method further includes processing, using one or more machine learning algorithms, the initial data to identify patterns between the blood glucose levels of the user, and the one or more of nutrition consumed by the user, times of day associated with checking the blood glucose levels of the user, times of day associated with the nutrition consumed by the user, sleep of the user, exercise performed by the user, medication consumed by the user, and mood of the user.

* * * * *